United States Patent [19]
Munderloh

[11] Patent Number: 6,082,204
[45] Date of Patent: Jul. 4, 2000

[54] TITRATION METHOD USING A SYRINGE

[76] Inventor: Neil Munderloh, 26 Vasco Dr., Mill Valley, Calif. 94941

[21] Appl. No.: 09/215,350

[22] Filed: Dec. 18, 1998

[51] Int. Cl.[7] .................................................. G01N 1/00
[52] U.S. Cl. ......................................................... 73/864.21
[58] Field of Search ........................... 73/864.13, 864.16, 73/864.81, 864.87, 864.21; 366/140; 422/75–77

[56] References Cited

U.S. PATENT DOCUMENTS

| | | |
|---|---|---|
| 3,410,664 | 11/1968 | Fielding ....................... 422/75 |
| 4,117,728 | 10/1978 | Johnson ..................... 73/864.18 |
| 4,339,317 | 7/1982 | Meiattini et al. . |
| 4,360,662 | 11/1982 | Williams . |
| 5,045,284 | 9/1991 | Smith et al. ................... 422/75 |
| 5,340,541 | 8/1994 | Jackson et al. . |
| 5,364,596 | 11/1994 | Magnussen, Jr. et al. ...... 73/864.18 |
| 5,707,848 | 1/1998 | Bryan et al. . |
| 5,817,954 | 10/1998 | Kahng et al. . |

*Primary Examiner*—Robert Raevis

[57] ABSTRACT

The present invention provides a method of titration using a syringe. In the method a sample is drawn into a syringe through a single bore needle; and a titrant is drawn into the syringe through the single bore needle until an end point is reached.

13 Claims, 2 Drawing Sheets

TITRATION METHOD USING A SYRINGE

FIELD OF THE INVENTION

This invention relates to the quantitative chemical analysis of liquids by means of volumetric titration, and aims to provide a device that is more compact, rugged, and easier to use than the presently available apparatus, while maintaining accuracy of measurement.

DESCRIPTION OF THE PRIOR ART

The analysis of fluids for a specific chemical constituent is often accomplished by a procedure known as titration, in which a standard solution is mixed in increments with a sample to which has been added a color-forming indicator so that a marked color change occurs at the point where the amount of standard solution just neutralizes all of the constituent present in the sample. At this endpoint, the amount of the unknown constituent in the sample may be ascertained from the amount of standard solution used.

The basic apparatus used for titrations has hardly changed since the beginning, and remains cumbersome and difficult to use. The unknown is delivered to a titration flask with a pipette, then standard is added by means of a burette until the endpoint is reached. Specifically, it suffers from the following disadvantages:

a) The apparatus is of multiple pieces. At a minimum, six pieces are required: a pipette, a burette, a burette stand, a burette clamp, a titration flask, and a funnel.
b) The apparatus is expensive. The minimum cost is about 150 dollars for the assemblage above.
c) The apparatus is bulky and difficult to store. The pipette, burette, and stand are all of substantial length.
d) The burette, pipette, and titration flask are made of glass and are easily broken.
e) The insides of the pipette and burette must be kept scrupulously clean to avoid drainage errors. This may require the use of dangerous or toxic cleaning agents.
f) The burette must be rinsed before use with the standard. This takes time and wastes standard. Also, standard remaining in the burette at the end of a series of titrations must be discarded.
g) Because liquids wet the insides of the pipette and burette, time must be allowed for drainage of these surfaces.
h) Burette measurements are made from the position of the meniscus. The meniscus is curved and is difficult to view. If viewed from an angle, a paraflax error may be made.
i) A small amount of unknown or standard may be splashed on the side of the titration flask. The titration must be paused to wash down this deposit, or a titration error will occur.
j) Any partial droplet on the tip of the burette is shown by burette reading as having been delivered, but has not been delivered to the titration flask. For best accuracy, it must be washed off into the titration flask.
k) The contents of the flask must be mixed by swirling. Therefore, two hands are required, one to control delivery from the burette, the other to swirl the flask. This may be tiring to the operator.
l) The operator must add precisely the right of amount of standard to achieve the endpoint. One must proceed cautiously or too much standard will be added, overshooting the endpoint. A good deal of time may be consumed doing a titration because of fear of overshooting the endpoint. This is especially true for an inexperienced operator. If the end point is overshot, the operator must then repeat the titration, or live with a less than optimum result.
m) Because the apparatus is open to the atmosphere, it is not suitable for titration of moisture sensitive, air sensitive, or volatile substances.
n) The apparatus is most accurate when a substantial portion of the contents of the burette is used for a titration. Therefore, to attain the required accuracy, it may be necessary to repeat the titration using a different amount of unknown, either by using a different pipette or by quantitatively diluting the unknown; or it may be necessary to use a standard of greater or lesser strength.
o) It is sometimes advantageous or necessary to perform reverse titrations, where the standard is titrated with the unknown. It is very inconvenient to do a series of reverse titrations, as the buret must be drained and filled with each new unknown.
p) The apparatus is not suitable for field use. A level work surface is required.
q) A computation of the amount of unknown must be made.

Improvements have been made upon the basic apparatus. The glassware may be replaced by plastic. The burette can be arranged so that it is automatically filled. The burette may be replace by a dispenser with digital readout. Stirring may be done with a magnetic stirrer and stir bar. However, the basic manipulations remain the same, with the result that performing a titration remains a complex and time consuming matter. Simpler methods using drop counting have been described and are used, however they are of limited accuracy.

Automated analyzers have been developed, however they are expensive and are best used for the analysis of many similar samples. They are not suited for field or educational use, or the analysis of a small number of samples. U.S. Pat. No. 5,817,954 issued to Kahng et. al. on Oct. 6, 1998, shows how the apparatus for automatic titration can be simplified, using some of the same ideas as the present patent.

OBJECTS OF THE INVENTION

It is the object of this invention to provide an apparatus and technique for titration that is superior to the existing apparatus. Specifically, some advantages are:

a) The apparatus is of a single piece.
b) The apparatus is of low cost. The cost of manufacture is substantially less than the existing apparatus.
c) The apparatus is compact and easy to store.
d) The apparatus is of rugged construction and not easily damaged.
e) The apparatus is easily cleaned with a minimal amount of water or other liquid.
f) No standard is wasted in rinsing the apparatus before use. The apparatus may be made of such a size that lesser amounts of standard and unknown are required, compared to the standard apparatus.
g) No time for the drainage of surfaces is required.
h) The amounts of unknown and standard are read from a ruled scale, with or without vernier, or from a digital display. Reading of the position of a meniscus is eliminated.
i) There is no concern about any amount of unknown or standard remaining unmixed.
j) The correction for standard measured but not mixed is small and of constant value.
k) Mixing is accomplished by a stirrer, and no manual mixing is needed.
l) There is very good indication of the nearness to the endpoint, and the adjustment to the endpoint is rapid and easily done. Therefore, the time required to do a titration is much reduced.

m) The apparatus is closed to the atmosphere and is suitable for the titration of moisture or air sensitive substances.
n) A large range of concentrations of unknown can be analyzed using a given strength of standard without undue loss of accuracy.
o) Reverse titrations are easily done.
p) The apparatus is suitable for for field use. A minimal work surface is required.
q) The apparatus is easily customized or programed so that the results of titrations of a given sort can be directly read from the scale or digital display, with no computation required.

Other objects and advantages will become apparent from the specifications, drawings, and description.

DESCRIPTION OF THE PREFERRED EMBODIMENT

Figure 1:
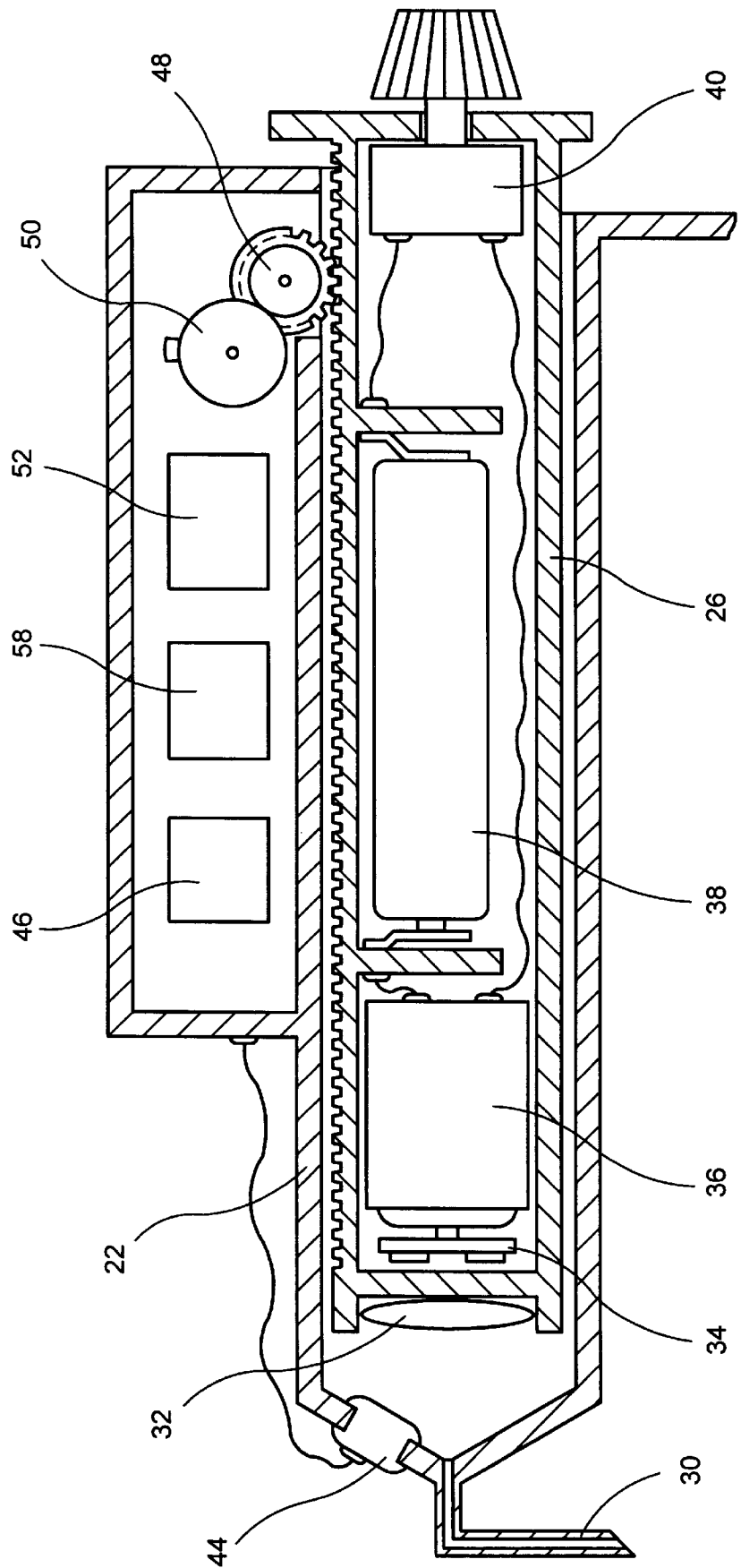
FIG. 1 shows a section view of one embodiment of the apparatus of the invention.
Figure 2:
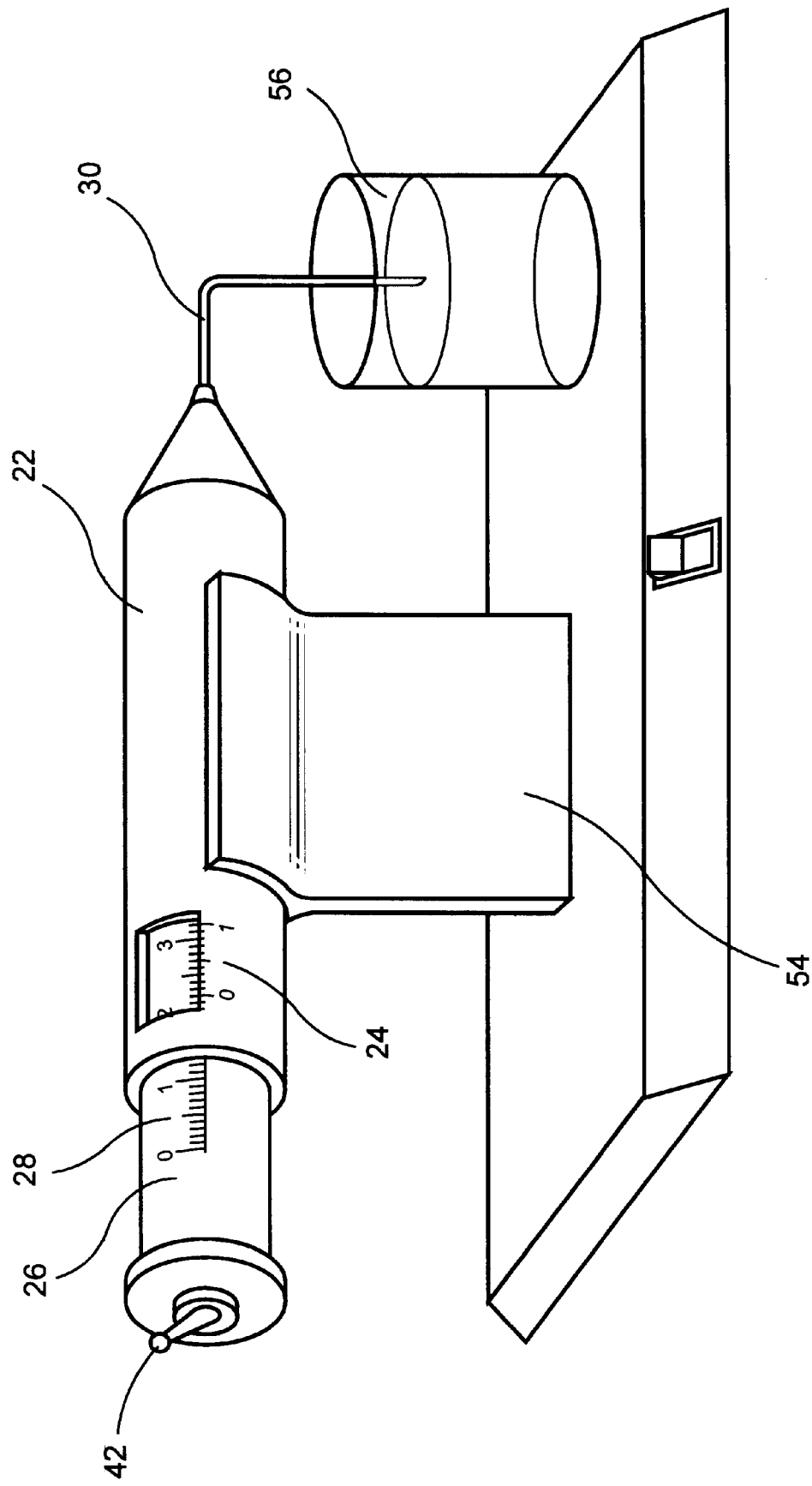
FIG. 2 shows a perspective view of another embodiment of the invention.

The preferred embodiments of the invention will hereinafter be described in conjunction with the appended drawings, where like designations denote like elements, and in which: 22 syringe barrel 24 vernier scale 26 syringe plunger 28 scale 30 needle 32 magnetic stir bar 34 magnets 36 electric motor 38 battery 40 switch with speed control 42 off/on switch 44 sensor 46 meter for sensor 48 thumb wheel 50 displacement sensor 52 volume display 54 holder 56 beaker 58 microprocessor with controls and display A syringe barrel 22 is constructed of material resistant to the chemicals used during the titration. Glass and various plastics are suitable. A needle 30 is attached to the syringe barrel 22 by a fitting, or it may be cemented in place. The needle is generally of stainless steel, but small bore plastic tubing may also be used. The inside bore of the needle should be as small in bore as possible without unduly restricting the uptake and discharge of the standard and unknown. The syringe barrel 22 may also have an opening for attachment of a sensor 44, located at the base of the barrel 22 near the syringe inlet. Placement of the sensor near the inlet is important because when placed there, it can give information about the approach of the endpoint. The sensor is most commonly a pH electrode. Sensor 42 is connected to a meter for sensor 46 which may be an integral part of the titration apparatus, A vernier scale 24 imprinted upon barrel 22 is used in conjunction with a scale 28 imprinted on the plunger 26 to read the volumes used. For less accurate work, a vernier is not necessary, and a single mark on the barrel will suffice. Because it is the proportion of unknown to standard that is of interest, the divisions of the scale need not correspond to any standard unit of volume. Rather, they are chosen for maximum readability. Division into centimeters and subdivision into millimeters is a good choice. A displacement sensor 50 connected to volume display 52 may also be used to measure the volumes of unknown and standard. These sensors are in common use, the most basic application being a calipers with digital readout.

The syringe plunger 26 is constructed of materials of suitable mechanical and chemical resistant properties. The portion of the plunger that will be in contact with the liquids must be resistant to the chemicals used. Teflon, polyethylene, and polypropylene are suitable materials. The plunger is machined to provide a leak-proof seal to syringe barrel 22, or may have a groove fitted for an o-ring or rings which provide the seal. The tightness of fit of plunger 26 in barrel 22 is sufficient as to prevent inadvertent movement of plunger 26. The plunger may also have a rough surface or rack to be used with a thumb wheel 48 to provide a means of fine movement of the plunger. Small movements of plunger 26 are necessary to get exactly to the endpoint. A magnetic stir bar 32 is located within the syringe.

The magnetic stir bar 32 is spun by drive magnets 34 which are spun by a electric motor 36. Electric motor 36 is powered by a battery 38, and controlled by a switch with speed control 40 or off/on switch 42. Alternately, the stir bar is controlled by a plurality of NS switched electromagnets, a known method. The stir bar must spin at a controlled rate, suitable as to allow easy addition of standard to the endpoint, as explained below.

A microprocessor with controls and display 58 may be electrically connected to displacement sensor 50. The microprocessor may be used to record the volume information, the strength of the standard, and to calculate the strength of the unknown. A holder 54 may be used to store the apparatus between uses, to charge the battery between uses, and to hold the apparatus in a fixed relationship to the unknown or standard in a beaker 56 during the titration.

The apparatus is first rinsed with water or other suitable liquid and the syringe plunger is positioned at or near the bottom. The small amount of liquid remaining in the syringe will not interfere with the titration. The beginning position is read. The needle tip is then wiped free of any adhering liquid. The syringe is held in a generally horizontal position, and the tip of the needle placed in a sample of the unknown. If the endpoint is to be detected by means of a color change, the addition of a small amount of an indicator to either the standard or unknown is generally necessary. A volume of the unknown is drawn into the syringe. The needle is withdrawn, wiped clean of unknown, and the volume read from the scale and vernier. The stirrer is then turned on. The needle is then placed in a sample of the standard and the standard is drawn up until the endpoint is reached. The rate of stirring is such that mixing is sufficiently slow so the the nearness of the endpoint can be easily ascertained, either by a change in color in the region near the inlet. or by a change in the sensor readout, the sensor being placed near the inlet. The importance of a proper rate of mixing and how this makes it easy to rapidly adjust to the endpoint cannot be overemphasized. If the mixing rate is too rapid, there will be little notice of the approach of the endpoint. If the mixing rate is too slow, excessive time is spent waiting for mixing to become complete. The small movements necessary to get exactly to the endpoint are more easily made if a thumb wheel or other means is used. At the end of the titration, the amount of standard is read. A calculation using the amount of unknown, the amount of standard, and the strength of the standard is done to give the strength of the unknown. For the most accurate work, a correction for the amount of standard left in the syringe is made. All liquid is expelled from the syringe and the apparatus is ready for the next titration.

If a series of titrations of a a given type is planned and a standard of consistent strength is available, a scale may be selected that has a mark showing the amount of unknown to be drawn up, and that will directly read the concentration of the unknown at the end of the titration, making a calculation unnecessary. For example the apparatus can be used to determine the titratable acidity of a wine, or the grape juice or other juice from which a wine is to be made. The syringe is equipped with a mark indicating the amount of unknown to be drawn up. The titration is done with a standard base solution until the endpoint is reached. Marks on the syringe plunger show directly the titratable acidity in any desired units. Thus a series of removable scales can be used with the same plunger to perform different standardized titrations.

Thus the reader will see that the titration apparatus of the invention provides a highly compact and easy to use device with many advantages over existing apparatus.

The apparatus is suitable for almost any type of volumetric titration, with the exception of those which evolve a gas, or form a precipitate which would clog the needle. The apparatus as described titrates a liquid with a liquid. A solid can be titrated if it is dissolved and drawn up in its entirety. The apparatus could also find use in the compounding of solutions, especially those that require a titration.

The accuracy attainable is limited principally by the quality of construction and the readability of the volumes. The apparatus will be most accurate when the full volume of the syringe is used, and the amounts of unknown and standard are equal. For example, with a vernier scale and a syringe travel of 70 millimeters, the unknown and the standard could each be read to 0.1 of 35 millimeters, leading to a potential accuracy of about 0.5% for the titration. If the amount of unknown is 10% of the amount of the standard, or the reverse, the liquid drawn up in lesser amount could be read to 0.1 of 7 millimeters, leading to a potential accuracy of about 1.4%. Thus, a large range of unknowns can be analyzed with a given standard without great loss of accuracy. If a displacement sensor with digital readout is fitted, the accuracy of reading is increased, as these sensors can detect a change in position of as little as 0.01 millimeter.

While the above description contains many specificities, these should not be construed as limitations on the scope of the invention, but rather as an exemplification of one preferred embodiment thereof. Many other variations are possible. For example, the movement of the plunger could be controlled by means of a motor. The stir bar could be driven by NS switched electromagnets located outside the syringe, either fixed at the bottom of the plunger, or following the movement of the plunger. The needle could be straight, and the syringe operated in a vertical position. The scale could be on the barrel and the vernier on the plunger. The stirrer could be powered by AC current instead of a battery. Accordingly, the scope of the invention should be determined not by the embodiments illustrated, but by the appended claims and their legal equivalents.

I claim:

1. A method of volumetric titration of an analyte in a sample, said method comprising:

(a) drawing said sample into a syringe through a single bore needle; and (b) drawing a titrant into said syringe through said single bore needle until an endpoint is reached.

2. The method in accordance with claim 1 further comprising:

(c) determining the concentration of said analyte in said sample from the amount of titrant drawn into said syringe at said endpoint.

3. The method in accordance with claim 1, wherein said syringe further comprises a stirring means for mixing the contents of said syringe.

4. The method in accordance with claim 3, wherein said stirring means is turned on prior to step (b).

5. The method in accordance with claim 1, wherein said syringe further comprises a sensor.

6. The method in accordance with claim 5, wherein said sensor is a pH sensor.

7. The method in accordance with claim 1, wherein said syringe further comprises a vernier scale.

8. The method in accordance with claim 1, wherein said syringe further comprises a digital readout.

9. The method in accordance with claim 1, wherein said syringe further comprises a thumb wheel for fine movement control.

10. The method in accordance with claim 1, wherein said endpoint is a color change.

11. The method in accordance with claim 10, wherein an indicator is added to said sample.

12. The method in accordance with claim 10, wherein an indicator is added to said titrant.

13. A method of volumetric titration of an analyte in a sample, said method comprising:

(a) drawing a titrant into a syringe through a single bore needle; and (b) drawing said sample into said syringe through said single bore needle until an endpoint is reached.

* * * * *